United States Patent [19]
Park et al.

[11] Patent Number: 5,605,612
[45] Date of Patent: Feb. 25, 1997

[54] GAS SENSOR AND MANUFACTURING METHOD OF THE SAME

[75] Inventors: Hyeon S. Park, Seoul; Kyu C. Lee, Shungcheongbuk-do; Chul H. Kwon, Chungcheongbuk-do; Dong H. Yun, Chungcheongbuk-do; Hyun W. Shin, Chungcheongbuk-do; Hyung K. Hong, Chungcheongbuk-do, all of Rep. of Korea

[73] Assignee: Goldstar Electron Co., Ltd., Chungcheongbuk-do, Rep. of Korea

[21] Appl. No.: 337,065

[22] Filed: Nov. 10, 1994

[30] Foreign Application Priority Data

Nov. 11, 1993 [KR] Rep. of Korea ............... 1993-23897
Mar. 15, 1994 [KR] Rep. of Korea ............... 1994-5132

[51] Int. Cl.⁶ .................................................. G01N 27/26
[52] U.S. Cl. .......................... 204/429; 422/83; 422/94; 422/97; 422/98; 436/153; 73/31.05; 73/31.06; 338/25; 338/34; 338/308; 338/314; 437/51; 437/60; 437/184; 437/187
[58] Field of Search ................. 422/83, 98, 94, 422/90, 97; 204/429, 426, 425; 437/51, 60, 918, 187, 184; 338/25, 34, 307, 308, 309, 314; 73/31.05, 31.06; 436/149, 153, 184

[56] References Cited

U.S. PATENT DOCUMENTS

| | | | |
|---|---|---|---|
| 4,225,410 | 9/1980 | Pace | 422/98 |
| 5,003,812 | 4/1991 | Yagawara et al. | 422/98 |
| 5,187,084 | 2/1993 | Hallsby | 435/91 |
| 5,287,752 | 2/1994 | Den Boer | 73/861.04 |
| 5,302,935 | 4/1994 | Chatterjee | 338/34 |
| 5,345,213 | 9/1994 | Semancik et al. | 338/34 |

Primary Examiner—Bruce F. Bell
Attorney, Agent, or Firm—John P. White

[57] ABSTRACT

A thin-film gas sensor and manufacturing method of the same is disclosed which includes a silicon substrate; an insulating layer formed on the surface of the silicon substrate; a heater formed in zigzag on the surface of said insulating layer; a temperature sensor formed in zigzag on the surface of the insulating layer in parallel with the heater; an interlayer insulating layer for electrically insulating the heater and temperature sensor formed on the insulating layer; a plurality of electrodes formed on the interlayer insulating layer placed between the heater and temperature sensor; a plurality of pairs of gas sensing layers disposed in an array on the electrodes and for reacting on detected gas; and a plurality of gas shielding layers formed on one gas sensing layer out of the pair of gas sensing layers and for shielding the detected gas so that the gas sensing layers do not react on the detected gas.

12 Claims, 13 Drawing Sheets

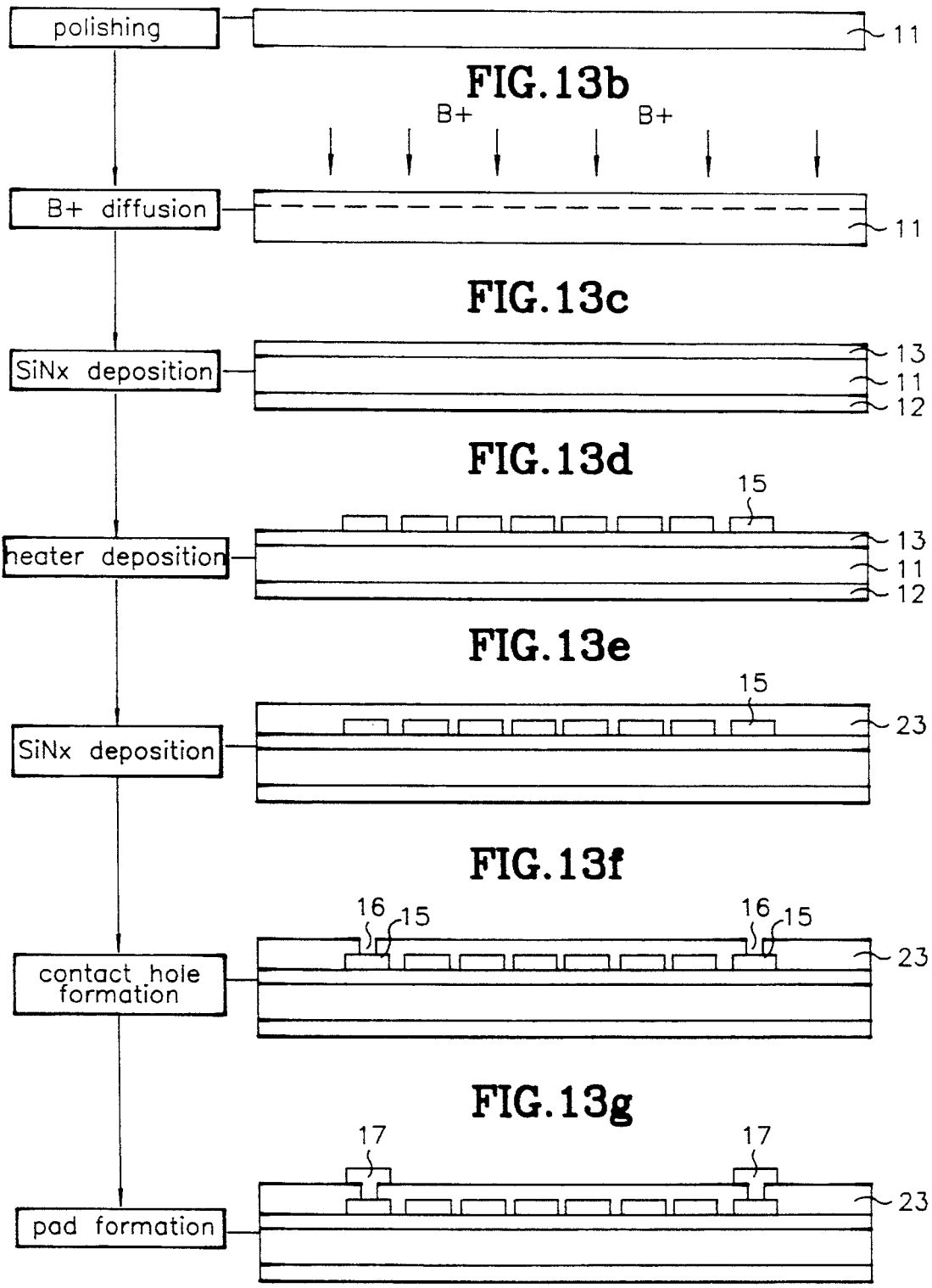

GAS SENSOR AND MANUFACTURING METHOD OF THE SAME

BACKGROUND OF THE INVENTION

The present invention relates to a thin film semiconductor gas sensor and manufacturing method of the same.

The gas sensor using metal oxide semiconductor, resistance-type gas sensor in which gas sensing material is coated on the ceramic substrate is widely used.

This resistance-type gas sensor is a thick-film sensor. FIG. 1 is a cross-sectional view of the gas sensor while FIGS. 2a & 2b are plan views of an electrode and a heater of the gas sensor.

As shown in FIG. 1, in the thick-film gas sensor, the electrode 1 to read an electric signal and gas sensing layer 2 which could react with detected gas are formed on the front surface of the a ceramic substrate 4. While, a heater 3 is formed on the back surface of the ceramic substrate 4 for heating gas sensing layer 2 to a predetermined temperature to enhance the reaction of the gas sensing layer 2 with detected gas. At this time, the ceramic substrate 4 is usually manufactured with alumina ($Al_2O_3$) substrate of about 0.635 mm thick or alumina cylinder.

FIGS. 2a and 2b are plan view of the electrode 1 and the heater 3, in which the resistance-type gas sensor is formed on the back surface of the ceramic substrate 4 made of alumina and the heater 3 is formed by coating conductive material by screen printing method and calcining at high temperature. As for the conductive material for manufacturing the heater, $RuO_2$-based material, Ni—Cr-based material, W-Pt-based material, etc. were used.

The electrode 1 is formed by coating conductive material such as Pt on the front surface of the ceramic substrate 4 using screen printing method and then calcining at high temperature. The conductive material for the heater or electrode should have an appropriate viscosity for applying screen printing method and maintain viscous solution state in which various materials are mixed, in order to easily adhere to the substrate.

The gas sensing layer 2 having a thickness of from about several μm to several tens μm is formed by coating a mixture-type powder of gas sensing material and catalyst and a paste homogeneously mixed with organic solvent, on the ceramic substrate 4 and between the electrodes 2 by screen printing method and then calcining at 300°–1,000° C. to give the gas sensor.

The powder used as a gas sensing material of the gas sensing layer 2 is obtained by coprecipitation or is fine and homogeneous conventionally used powder. Generally, various material could be used for gas sensing layer 2. For example, $SnO_2$ is usually used for detecting flammable gas, $WO_3$ is for detecting alcohols and metal oxide semiconductor such as ZnO is for detecting various gas. Catalyst is added to the gas sensing layer 2 for enhancing the reaction with the detecting gas. Noble metals such as Au, Pt, Pd, etc. in various states could be added to the gas sensing layer 2 as the catalyst.

The paste for the gas sensing layer is prepared by pulverizing the gas sensing material and mixing thus obtained powder with organic solvent. The powder for the gas sensing material is prepared as follows.

First, adding an appropriate amount of catalyst to the gas sensing material and ball-milling the mixture to mix the gas sensing material and the catalyst homogeneously. That is, after mixing the gas sensing material with the catalyst in a constant ratio the mixture is ball-milled with alcohol and balls of appropriate size. The balls are separated from the powder through sieving the ball-milled mixture. The powder is sufficiently dried in an infrared drying apparatus to evaporate the alcohols. At this time, the catalyst should not be allowed to lump together to precipitate.

The dried powder is pulverized to an appropriate size using agate mortar, and then the powder is mixed with alcohols and balls to further pulverize the powder even finer. The pulverized powder is sieved to separate the balls and dried using an infrared drier to evaporate the alcohols. The dried powder is pulverized again in an agate mortar to obtain the final powder including catalyst.

The reason why the gas sensing material is pulverized to such a fine powder is to increase contacting surface area during the reaction with the detected gas and to increase the viscosity.

In the conventional gas sensor, oxides such as CuO are used as the catalyst, and when the adhesion state of the ceramic substrate and the gas sensing layer is not good, $SiO_2$, $Al_2O_3$ or etc. are added to the gas sensing material to compensate. $SiO_2$, $Al_2O_3$ or etc. also could be added to the gas sensing material in the same method as the catalyst addition to the gas sensing material.

Gas sensing material mixed with various materials is pasted with the organic solvent to obtain a gas sensing material paste having appropriate viscosity which could be easily applied to the screen printing method. As for the solvent, it is a solution prepared by dissolving 5–10% of ethylcellosolve in α-terpenol at 80° C. with stirring.

FIG. 3 is a perspective view of the conventional sintered gas sensor.

In the ceramic cylinder-type gas sensor illustrated in FIG. 3, the gas sensing layer could not be formed by the screen printing method. Accordingly, gas sensing material, for example $SnO_2$ paste is coated on the surface of the cylindrical ceramic tube 5 using brush to form gas sensing layer 6. Both electrodes 7-1 and 7-2 and the heater which were manufactured through the sequential process of forming the electrodes and the heater were used after connecting them with lead wire.

The thus-obtained gas sensor as illustrated in the FIGS. 1–3 are called resistance-type semiconductor gas sensor and operation mechanism thereof is as follows.

The principle of sensing the detected gas of the gas sensing layer is as follows.

Initially, various gases such as oxygen in the air are chemically bonded on the surface of the gas sensing layer. The chemically bonded gases make bondage through electrons in the semiconductor state gas sensing layer.

Therefore, the gas sensing layer is deficient in electrons and the conductivity thereof decreases. That is, the resistance of the gas layer remarkably increases owing to the increase of the resistance.

In this state, if detected gas exists, the adsorbed gases on the surface of the gas sensing layer through chemical bond reacts with the detecting gas to produce other gas and simultaneously the electrons bonded with the adsorbed gases on the surface of the sensing layer separate again. Accordingly, the conductivity of the gas sensing layer increases while the resistance of the gas layer remarkably decreases.

That is to say, in the resistance-type semiconductor gas detecting sensor, the resistance of the gas sensor decreases if the gas under detection exists, while the resistance increases if the gas under detection does not exists.

In case of constructing electric circuit by connecting this gas sensor with the load resistance in series and applying constant voltage, the current flowing in the series circuit is low when the gas under detection does not exist and the resistance of the gas sensor is high, while the current flowing in the series circuit gradually increases when the concentration of the gas under detection increases and the resistance of the gas sensor gradually decreases. Accordingly, the voltage at the load resistance increases. That is, the voltage at the load resistance varies according to the gas concentration.

The heater provided in the metal oxide semiconductor gas sensor emits heat as the current flows and heats the gas sensing layer to a predetermined temperature. The reason why the gas sensing layer is heated to the predetermined temperature is that the gas sensing layer has high selectivity to some gases according to the coated material. That is, through activating the gas sensing layer and heating it to constant temperature, reaction with the gas under detection is facilitated and side effects caused by humidity and other gases other than the detected gases could be reduced and the selectivity to the detected gas could be increased. In addition, the response time to the detected gas of the gas sensing layer could be shortened. And a contaminant could be removed from the surface of the gas sensing layer when the surface of the gas sensing layer is exposed to other gases and contaminated.

In the above described thick film-type gas sensor, since the ceramic substrate is provided between the heater for heating the gas sensing layer and a gas sensing layer, an effective heating of the gas sensing layer is difficult owing to large heat loss. Moreover, since the ceramic substrate is thick and it is difficult to form the heater accurately through the screen printing method, the temperature distribution in the gas sensing layer is non-uniform and error thereof is large. Therefore, the gas sensor often mis-operates and its reliability become worse.

Meanwhile, in case of forming both of the electrode and the heater on the front surface of the ceramic substrate, the manufacturing process is complicated let alone local heating owing to the uneven heater and the ceramic substrate. Accordingly, the locally occurred high temperature region accelerates the deterioration of the gas sensing layer and this induces a serious problem of shortening the lifetime of the gas sensing layer along with the deterioration of the response characteristic of the gas sensor. Moreover, in case of manufacturing the gas sensor using the ceramic substrate, it is difficult to form plural gas sensors with various gas sensing materials on the same substrate. In order to manufacture plural gas sensors on the same substrate, repeated screen printing should be carried out. If repeated screen printing is carried out, since the adhesion strength between the gas sensing layer and the ceramic substrate is weak, previously the screen printed gas sensing layer deteriorates. And screen printing a plurality of gas sensing layers in accurate position is very difficult. Moreover, the thus manufactured gas sensor is large-sized and so power consumption becomes high. Practically, when packaging the device, the connection of the lead wire of the electrode and the heater to the fixing pin in the package is difficult.

Therefore, the conventional gas sensors usually consist of single gas sensor, and in this case, the problem of showing non-selectivity that the gas sensor reacts with various gases does not occur.

To solve the non-selectivity problem on the detected gas, a technique of forming a plurality of gas sensor on a silicon substrate using semiconductor technique is developed.

However, though the various problems could be solved when manufacturing the gas sensor of plurality of thin film by applying the semiconductor manufacturing technique, since each gas sensor has different operation temperature which varies according to the material of the gas sensing layer of the gas sensor, manufacturing method thereof and kind of the gas under detection, a separate heater should be provided. And since different electric power should be applied to each heater, the same number of sources of electric power to drive each heater are needed. That is, in order to drive a small array gas sensor, a plurality of seperate large-sized sources of electric power are needed.

Generally, the gas sensor when compared with other devices is liable to be affected by the ambient factor, gases as well as by other factors other than the gases such as humidity or temperature. Moreover, the initial resistance of the air of the gas sensing layer gradually varies through heating by the heater.

The initial resistance indicated by the sensor in the fresh air is the reference of all the information data when using the pattern recognition method which consists plurality of gas sensor in a chip on the same substrate to distinguish gases and to react with specific gas selectively. Therefore, when the change of the initial resistance according to the operation time is compensated, mis-operation of the sensor could be prevented owing to the error.

However, the conventional gas sensor does not have good selectivity and has serious problem of decreasing reliability owing to the mis-operation resulted from the change of the initial resistance through the external condition change with time or through heating by the internally provided heater.

SUMMARY OF THE INVENTION

Therefore, it is an object of the present invention to provide a thin-film gas sensor and manufacturing method thereof, which is formed in plurality on a silicon substrate by using a semiconductor device manufacturing technology.

It is another object of the present invention to provide a thin-film gas sensor and manufacturing method thereof where a heater and electrodes are uniformly and simultaneously formed over a silicon substrate, thereby preventing a gas sensing layer from being deteriorated due to high pressure generated locally, and enhancing a response characteristic.

It is still another object of the present invention to provide a high-performance thin-film gas sensor and manufacturing method thereof, which removes errors due to external environment and errors created by the variation of an initial resistance value due to the heating of an internal heater, thereby enhancing reliability and selectivity of the device.

It is yet another object of the present invention to provide an array thin-film gas sensor and manufacturing method thereof, in which a single heater satisfies various operation temperatures of the array gas sensor so that it can be driven only with one power device.

To accomplish the objects of the present invention, there is provided a thin-film gas sensor comprising: a silicon substrate; an insulating layer formed on the surface of the silicon substrate; a heater formed in zigzag on the surface of said insulating layer; a temperature sensor formed in zigzag on the surface of the insulating layer in parallel with the heater; an interlayer insulating layer for electrically insulating the heater and temperature sensor formed on the insulating layer; a plurality of electrodes formed on the interlayer insulating layer placed between the heater and temperature sensor; a plurality of pairs of gas sensing layers disposed in an array on the electrodes and for reacting on detected gas; and a plurality of gas shielding layers formed on one gas sensing layer out of the pair of gas sensing layers and for shielding the detected gas so that the gas sensing layers do not react on the detected gas.

In the embodiment, the heater may be constructed so that the respective gas sensing layers are heated at different operation temperatures. While the distance between lines of heater is kept constant, lines of a narrower width may be provided under the pair of gas sensing layers having a higher operation temperature, and lines of a broader width be provided under the pair of gas sensing layers having a lower operation temperature. While the width of lines of heater is kept constant, lines of narrower distance may be provided under the pair of gas sensing layers having a higher operation temperature, and lines of a broader distance be provided under the pair of gas sensing layers having a lower operation temperature. The heater may have narrower line width and line distance under the pair of gas sensing layers having a higher operation temperature, and have broader line width and line distance under the pair of gas sensing layers having a lower operation temperature.

Out of the pair of gas sensing layers, one on which the gas shielding layer is formed acts as a reference device, and the other acts as a gas sensing portion for reacting to the detected gas.

Out of the pair of gas sensing layers, the gas sensing layer acting as the reference device and the gas sensing layer acting as the gas sensing portion are made of the same gas sensing material.

The plurality of electrodes comprise: a plurality of common electrodes commonly connected to the gas sensing layer where the gas shielding layer is not formed and to the gas sensing layer where the gas shielding layer is formed; a plurality of first electrodes connected to the gas sensing layer where the gas shielding layer is not formed; and a plurality of second electrodes connected to the gas sensing layer where the gas shielding layer is formed.

To accomplish the objects of the present invention, there is provided a method of manufacturing a thin-film gas sensor comprising the steps of: forming an insulating layer on both sides of a silicon substrate; simultaneously forming a heater and a temperature sensor formed in zigzag on the insulating layer on the front surface of the silicon substrate; forming an interlayer insulating layer on the insulating layer where the temperature sensor and the heater are formed; forming a contact hole by exposing part of the heater and the temperature sensor; forming a pad for heater and a pad for temperature sensor on the interlayer insulating layer so that the contact hole comes into contact with the heater and the temperature sensor; forming a plurality of electrodes on the interlayer insulating layer excluding a portion where the pad for heater and the temperature sensor are formed; forming a plurality of pairs of gas sensing layers in an array form, on the interlayer insulating layer including the electrodes; forming a gas shielding layer only on one gas sensing layer of the respective pairs of gas sensing layers; etching the insulating layer formed on the back surface of the substrate, thereby exposing the insulating layer to the substrate; and etching the exposed substrate with the insulating layer being as a mask.

The step of forming a plurality of gas sensing layers comprises: coating a photoresist layer on the insulating layer where the electrodes and pad are formed; removing the photoresist layer placed on a corresponding electrode out of the plurality of electrodes; depositing a gas sensing material where Pd catalyst is contained in ZnO, by sputtering; removing the ZnO gas sensing material placed on the electrodes by lift off, to thereby form a pair of gas sensing layers made of ZnO only on a corresponding electrode where the photoresist layer is removed; re-coating a photoresist layer on the insulating layer where the electrodes and pad are formed; removing the photoresist layer placed on the electrode where the pair of ZnO gas sensing layers are formed, and on a nearby electrode; depositing a gas sensing material where Pd catalyst is contained in $SnO_2$, by sputtering; removing the $SnO_2$ gas sensing material on the electrodes by lift off, to thereby form a pair of gas sensing layers of $SnO_2$ only on the electrode where the photoresist layer is removed; coating a photoresist layer on the insulating layer where the electrodes and pad are formed; removing the photoresist layer placed on the electrode where the pair of $SnO_2$ gas sensing layers are formed, and on a nearby electrode; depositing a gas sensing material where Pd catalyst is contained in $WO_3$, by sputtering; removing the $WO_3$ gas sensing material on the electrodes by lift off, to thereby form a pair of gas sensing layers of $WO_3$ only on the electrode where the photoresist layer is removed;

BRIEF DESCRIPTION OF THE DRAWING

The above objects and advantages of the present invention will become more apparent by describing in detail a preferred embodiment thereof with reference to the attached drawings in which:

FIGS. 13a–13l illustrate a manufacturing process of the gas sensor shown in FIG. 11.

DETAILED DESCRIPTION OF THE INVENTION

Figure 1:
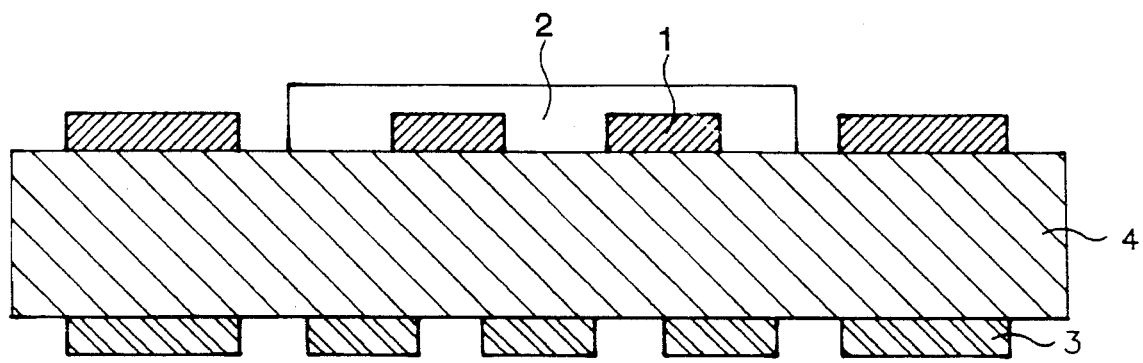
FIG. 1 illustrates the structure of a conventional thick-film gas sensor.
Figure 2A:
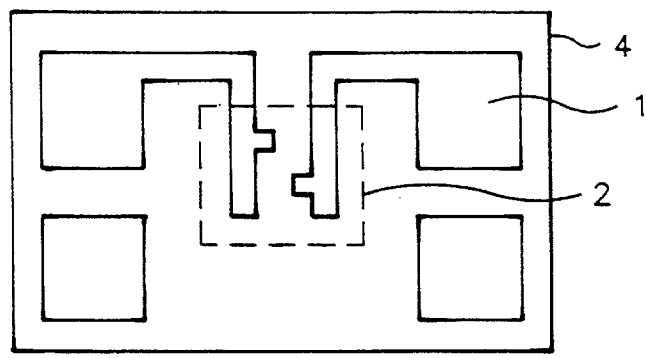
FIGS. 2a and 2b illustrate the respective plan structures of electrodes and heater of the thick-film gas sensor shown in FIG. 1.
Figure 2B:
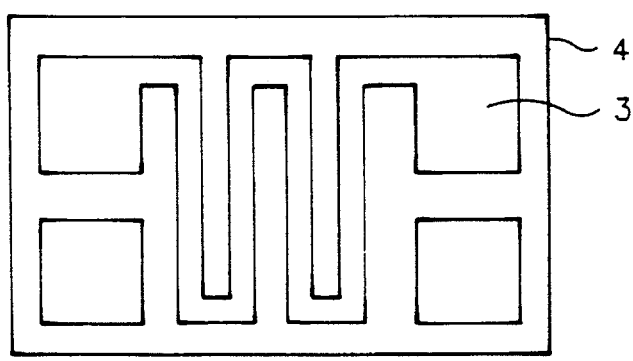
Figure 3:
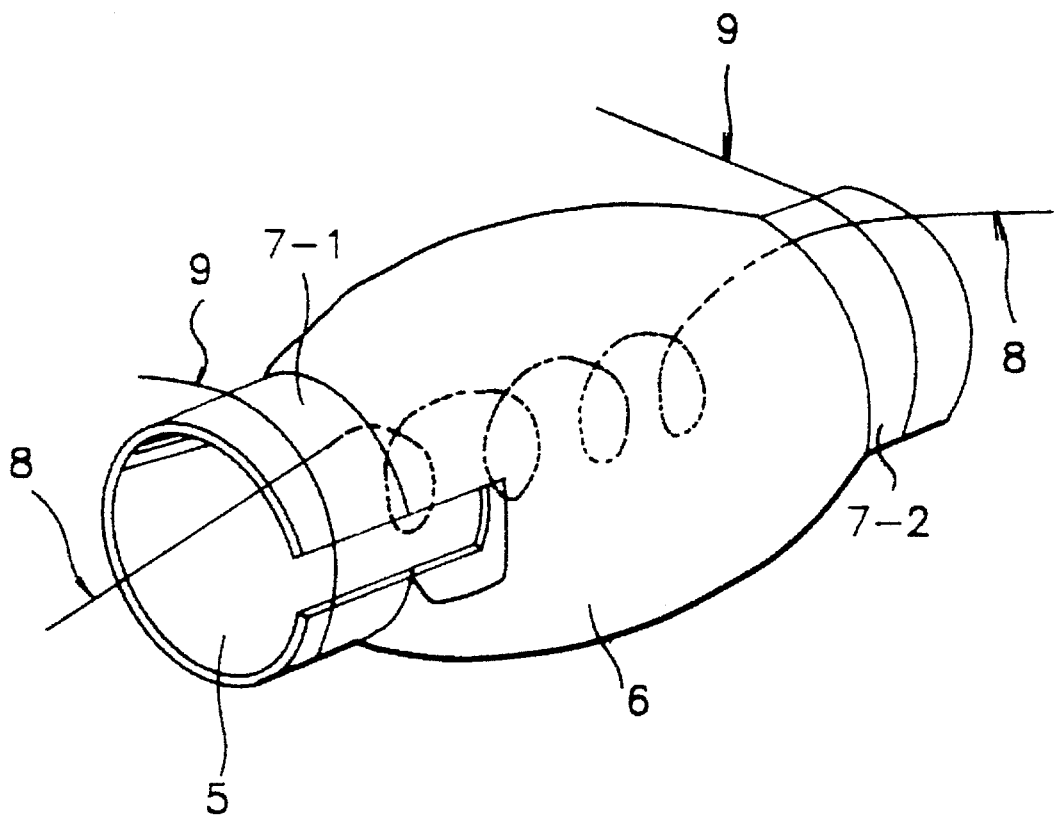
FIG. 3 illustrates the structure of a conventional sintered gas sensor.
Figure 4:
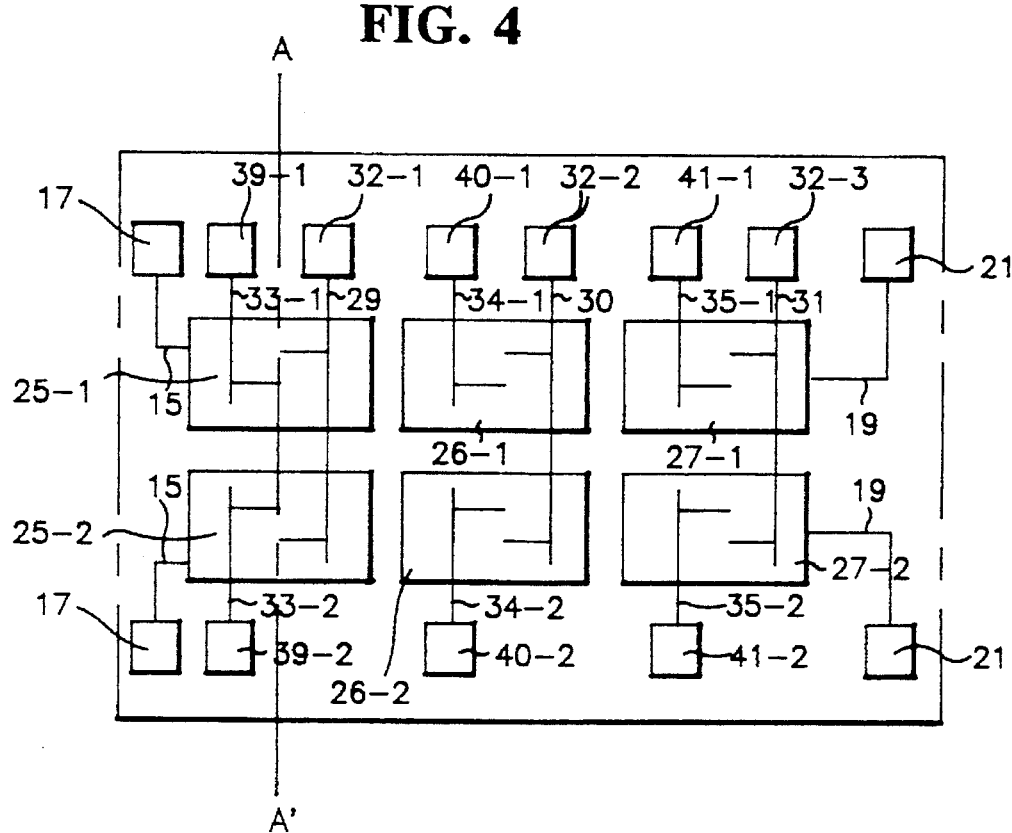
FIG. 4 illustrates the plan structure of one embodiment of a thin-film gas sensor of the present invention.
Figure 5:
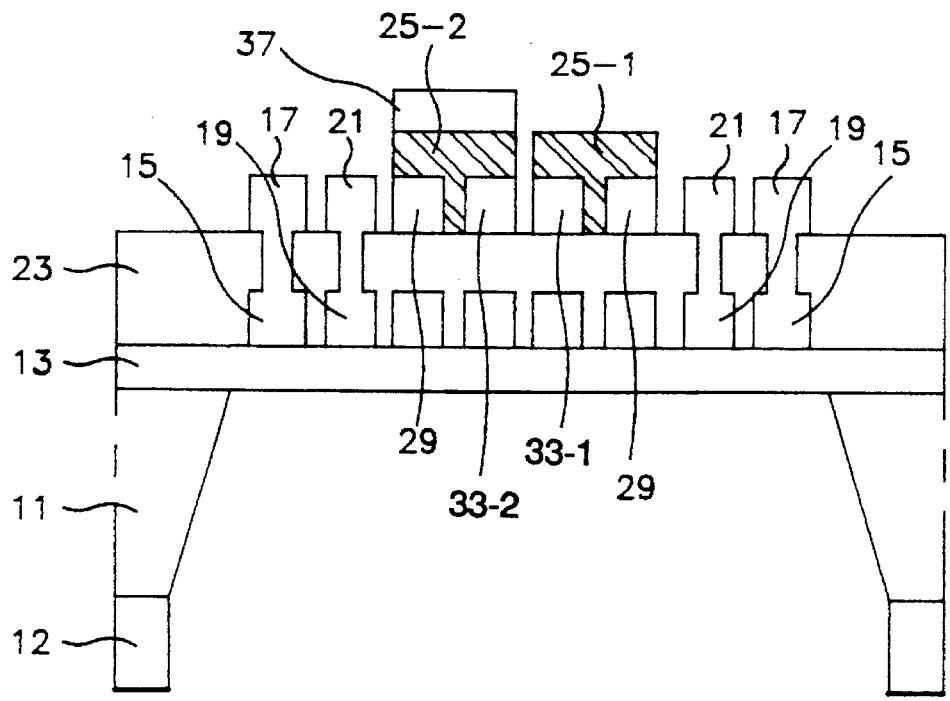
FIG. 5 illustrates the A-A' cross-sectional structure of the gas sensor shown in FIG. 4.

Referring to FIGS. 4 and 5, one embodiment of the gas sensor of the present invention comprises a silicon substrate 11, insulating layers 12 and 13 formed on the front and back surfaces of silicon substrate 11, a heater 15 formed on the surface of insulating layer 13 for support in zigzag, a temperature sensor 19 formed in zigzag on the surface of insulating layer 13 in parallel with heater 15, an interlayer insulating layer 23 for electrically insulating heater 15 and temperature sensor 19 formed on insulating layer 13, a plurality of electrodes formed on insulating layer 23 on heater 15 and temperature sensor 19, a plurality of gas sensing layers formed on the electrodes, and a plurality of gas shielding layers formed on part of the plurality of gas sensing layers and for shielding detected gas so that the gas sensing layers do not react on the detected gas.

Referring to FIG. 4, three pairs of gas sensing layers are formed on insulating layer 23 to thereby constitute an array of six gas sensors.

The gas sensing material of the first pair of gas sensing layers 25-1 and 25-2 is $SnO_2$. The gas sensing material of the second pair of gas sensing layers 26-1 and 26-2 is $WO_3$. The gas sensing material of the third pair of gas sensing layers 27-1 and 27-2 is ZnO. Out of the gas sensors, those in which the gas shielding layer is formed serve as a reference device portion, whereas those in which the gas shielding layer is not formed function as a gas sensing device portion.

The plurality of electrodes, made up of common electrodes and other electrodes, are formed under the respective gas sensing layers. A common electrode 29 is formed under the first pair of gas sensing layers 25-1 and 25-2. Electrodes 34-1 and 34-2 are formed on the respective gas sensing layers. In this manner, common electrodes 29-31 and electrodes (33-1, 33-2), (34-1, 34-2) and (35-1, 35-2) are respectively formed under the second and third pairs of gas sensing layers.

A manufacturing method for the embodiment of the present invention is roughly divided into a step of manufacturing a sputtering target and a step of manufacturing a device.

First, the step of manufacturing a sputtering target will be explained below.

The step of manufacturing a sputtering target is a process of making a gas sensing material target necessary in forming a gas sensing layer from the manufacturing process of the thin-film gas sensor. The step is carried out in the following sequence.

1) Powders of $SnO_2$, $WO_3$ and ZnO used as basic material of the target and various catalyst materials to be added thereto are mixed.

2) An adequate amount of ball and ethanol are mingled for ball milling for 24 hours so that the particle form and size of the powders are uniform.

3) The result is sufficiently dried in an infrared drying apparatus and the ethanol is evaporated.

4) The dried powders are pulverized in an agate mortar and strained out through a 100 mesh sieve so that the particle size of the powder becomes more homogeneous.

5) The result is calcined for several hours at 600° C. under $N_2$ atmosphere.

6) Foreign matters are removed through the calcination and stabilized powders are re-pulverized and strained out through a sieve.

7) The result is molded in a predetermined size by a compressing molding apparatus.

8) The result is sintered at 1,000°–1,600° C. in the molded state so that targets are manufactured for conditions of the gas sensing material for forming the gas sensing layer.

Subsequently, the device manufacturing process using the gas sensing material manufactured as above will be explained with reference to FIGS. 6a–6l.

Figure 6A:
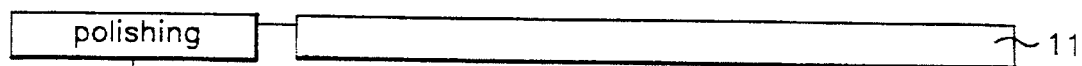
FIGS. 6a–6l illustrates a manufacturing process of the thin-film gas sensor of FIG. 4.
Figure 6B:
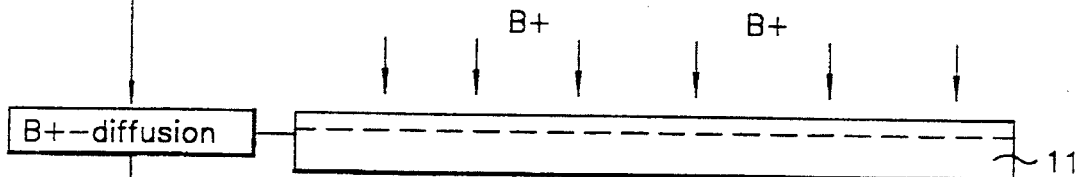

Referring to FIG. 6a, a silicon substrate 11 is p-type 100. Both sides of substrate 11 are polished so that the thickness of silicon substrate 11 is about 400 μm. Referring to FIG. 6b, boron is diffused to the depth of 2 μm from the surface of the substrate only on one side (front) of the polished silicon substrate. The boron diffused through the substrate acts as an etch stop in a succeeding substrate etching step.

Figure 6C:
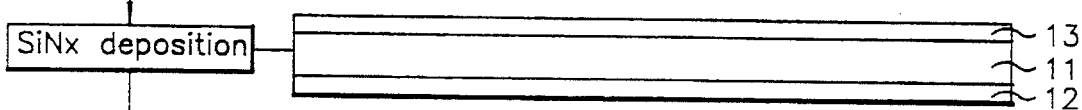

Referring to FIG. 6c, nitride layers 12 and 13 are uniformly deposited on both sides of silicon substrate 11 to the thickness of 3,000 Å by LPCVD. Here, nitride layer 13 formed on the front surface of the substrate through which boron is injected acts as a support layer, whereas nitride layer 12 formed on the back surface of the substrate acts as an etching mask in a succeeding etching step of the silicon substrate.

Figure 6D:
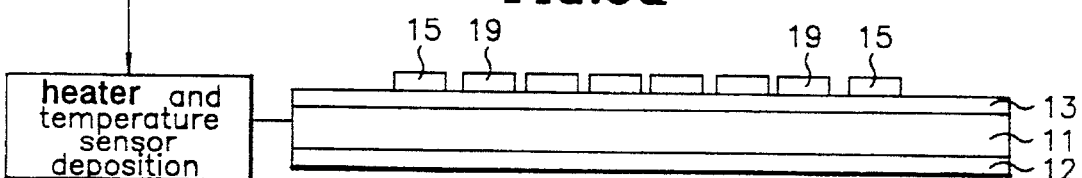

Referring to FIG. 6d, a photoresist layer (not shown) is coated on the overall surface of the substrate and photolithographed so that the photoresist layer on a portion where the heater and the temperature sensor are formed is removed to expose the substrate. Then, tantalum which is excellent in adhering to the nitride layer is deposited to the thickness of 500 Å under 7.5 mmT of pressure by sputtering, and platinum is deposited to as thick as 4,500 Å. The silicon substrate where tantalum and platinum are deposited is immersed into acetone so that unnecessary tantalum and platinum are removed by lift off using ultrasonic waves. By doing this, the photoresist layer is removed and tantalum and platinum are left only on the exposed substrate. Through this process, heater 15 and temperature sensor 19 for controlling the temperature of the heater are manufactured.

Figure 12A:
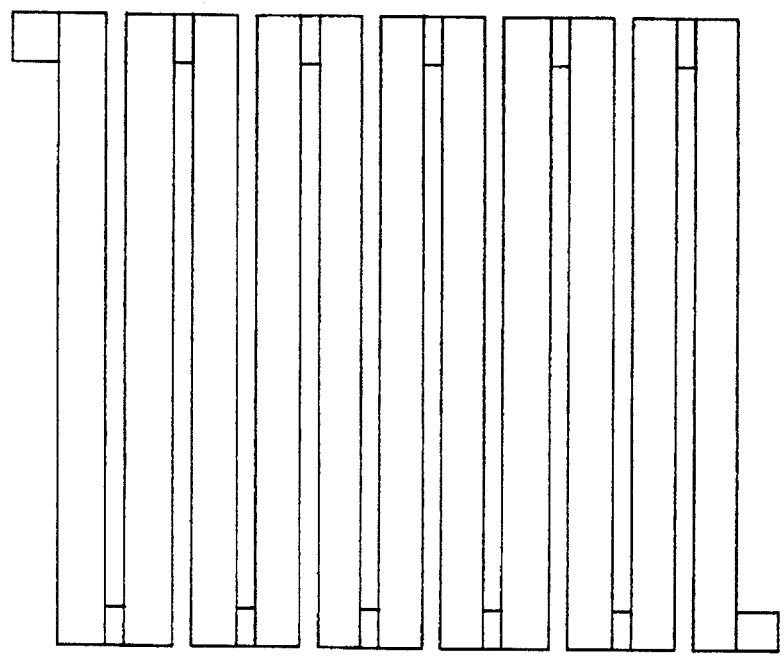
FIGS. 12a and 12b illustrate the structure of heater of the gas sensor of the present invention.
Figure 12B:
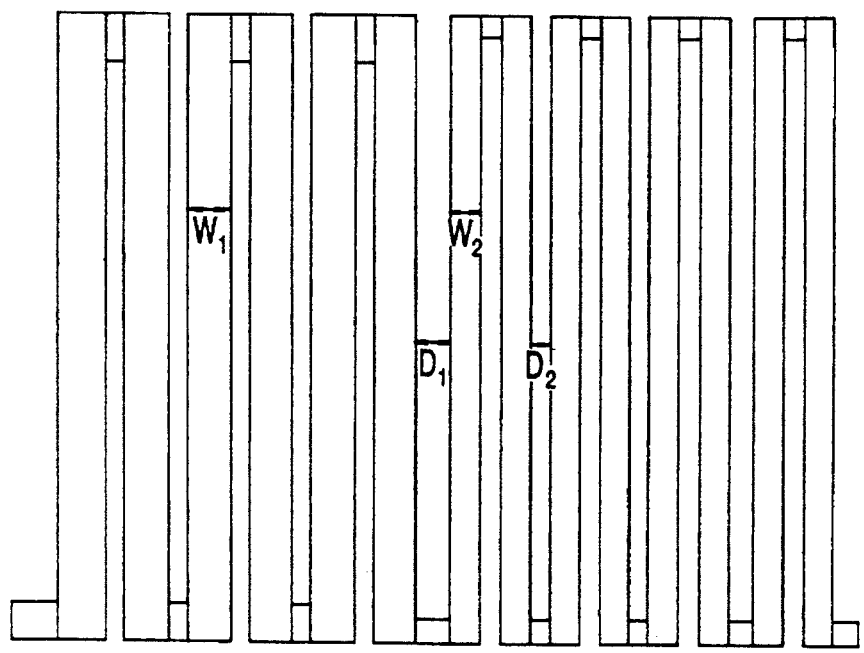

Heater 15, as shown in FIGS. 12a and 12b, is formed in zigzag on insulating layer 13 for support. Temperature sensor 19 is also formed in zigzag in the same manner as the heater. The heater and the temperature sensor are disposed in parallel on insulating layer 13.

Figure 6E:
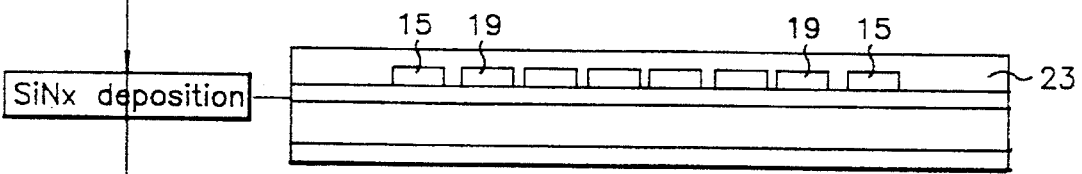

Referring to FIG. 6e, an insulating layer 23 for electrically insulating heater 15 and temperature sensor 19 and electrodes formed in a succeeding step is deposited on the front surface of the substrate where heater 15 and temperature sensor 19 are formed, as thick as 6,000 Å by sputtering. Insulating layer 23 is a nitride layer.

Figure 6F:
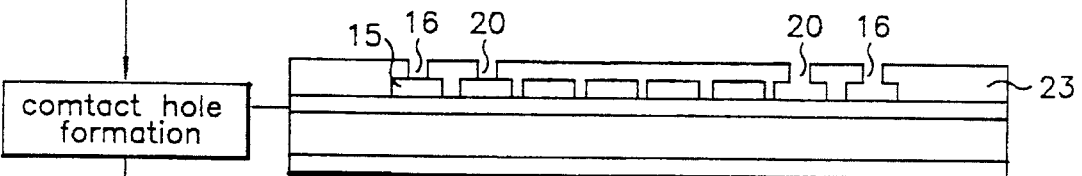

Referring to FIG. 6f illustrating a step of forming contact holes for forming pads for the heater and the temperature sensor, insulating layer 23 placed on heater 15 and temperature sensor 19 is removed by Reactive Ion Etching (RIE) which is a dry etching method, to thereby form contact holes 16 and 20.

Figure 6G:
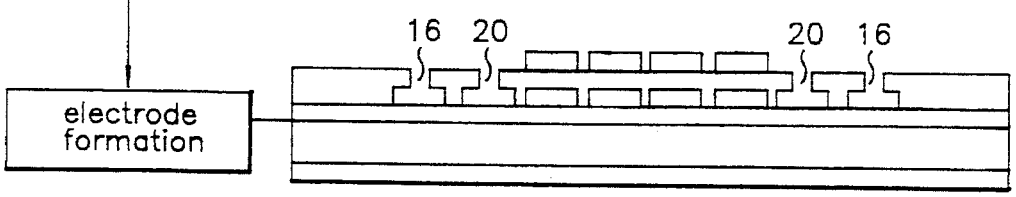
Figure 6H:
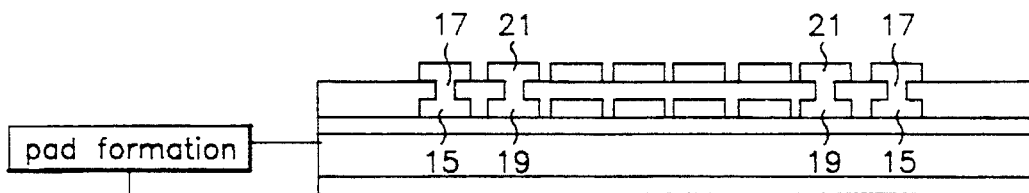
Figure 6H:
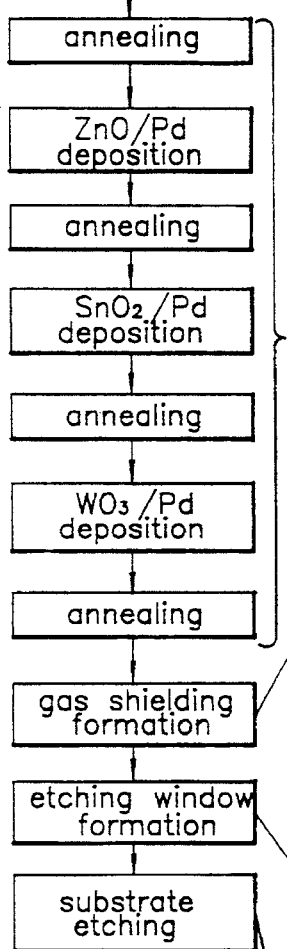

Referring to FIGS. 6g and 6h illustrating a step of forming electrodes and pads, tantalum and platinum are deposited by sputtering as thick as 500 Å and 4,500 Å, respectively, in the same manner as the heater and the temperature sensor. Similarly, a pad 17 for heater is formed so that it is electrically coupled to heater 15 via contact hole 16, and simultaneously, a pad 21 for temperature sensor is formed so that it is electrically connected to temperature sensor 19 via contact hole 20. This is the finish of metallization.

In this state, in order for the metal thin film to become dense and have a low resistance value for smooth flow of currents, heat treatment is performed for 30 minutes at 300°–800° C. in $N_2$ atmosphere.

Figure 6I:
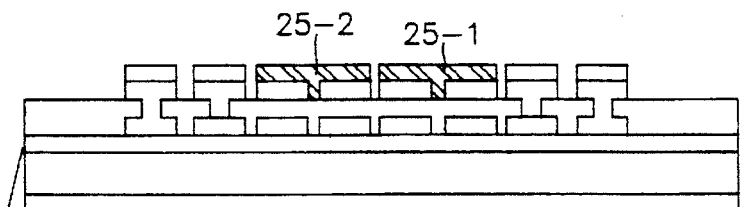

FIG. 6i illustrates a step of forming a plurality of gas sensing layer by using the gas sensing material manufactured in the sputtering target step. Three pairs are formed for the gas sensing layer and each pair is made of different materials.

The gas sensing layers are formed on corresponding electrodes in pairs. First, a photoresist layer (not shown) is coated on insulating layer 23 where the electrodes and pads are formed and the photoresist layer is removed on a corresponding electrode. A gas sensing material where Pd catalyst material is contained by 0–10% in ZnO is deposited thereon by sputtering.

The ZnO gas sensing material is removed by lift off so that a pair of gas sensing layers 25-1 and 25-2 made of ZnO are formed only on the corresponding electrode where the photoresist layer is removed.

Subsequently, in order for the structure of the gas sensing layers to become dense and to promote easy gas reaction, heat treatment is performed for several hours at 400°–800° C. in air. Near to the ZnO gas sensing layer pair, a gas sensing layer where Pd is contained by 0–10% in $SnO_2$ is deposited and thermally treated in the same manner as the ZnO gas sensing layer. A gas sensing material where Pd is contained by 0–10% in $WO_3$ is deposited and thermally treated near $SnO_2$ layer in the same manner as above. By doing this, six gas sensing layers all are formed. In another way, once heat treatment is allowable after all the gas sensing layers are formed.

Figure 6J:
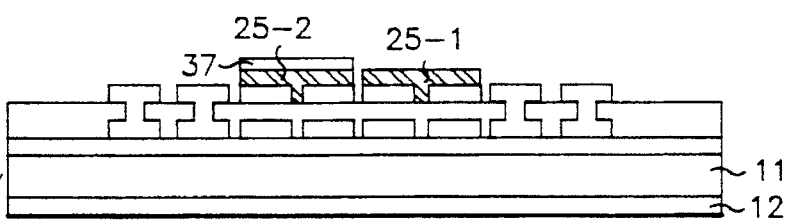

FIG. 6j illustrates a step of forming a gas shielding layer. A nitride layer is formed as thick as 10,000 Å by sputtering, to thereby form a gas shielding layer 37 for shielding the gas sensing layer serving as a reference device from coming into contact with detected gas.

Here, in order to use, as the reference device, one gas sensing layer out of a pair of gas sensing layers made of the same material, the gas shielding layer is formed. Of the pair of gas sensing layers, one layer is designed not to react to the gas and the resistance thereof is supposed to vary only according to the heat of the heater so that the gas sensing layer becomes a reference device having the same conditions as those of the other gas sensing layer where the gas shielding layer is not formed.

After the overall steps on the silicon substrate, in order to shield heat transmission to the side or bottom of the device and thereby minimize the power consumption of the heater, the silicon substrate which has a larger heat loss than the support layer is removed and alternately a diaphragm-structured silicon substrate is formed.

Figure 6K:
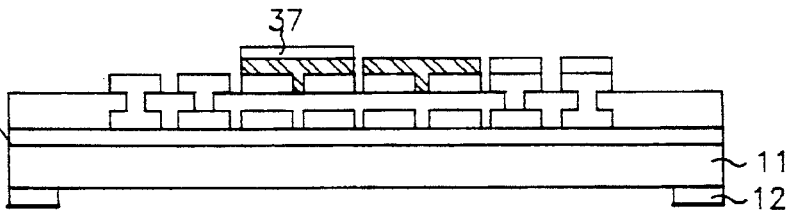
Figure 6L:
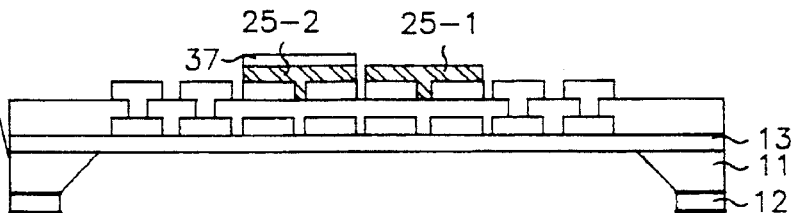

Specifically, insulating layer 12 formed on the back surface of the substrate is removed by RIE and the back surface of the silicon substrate to be etched is exposed as shown in FIG. 6k. KOH solution of excellent selectivity to the silicon and nitride layer is used and anisotropic etching is performed for 5–6 hours to etch the exposed silicon substrate. Here, if boron is diffused into the silicon substrate as in the above process, since the layer where boron is diffused serves as an etch stop, the silicon substrate is etched to the layer where boron is diffused. If boron is not diffused, the silicon substrate is etched until the insulating layer for support is exposed. This shields heat transmission to the side or bottom of the device. Therefore, the power consumption of the heater is minimized and the gas sensing layers can be efficiently heated to 300° C.

Figure 7:
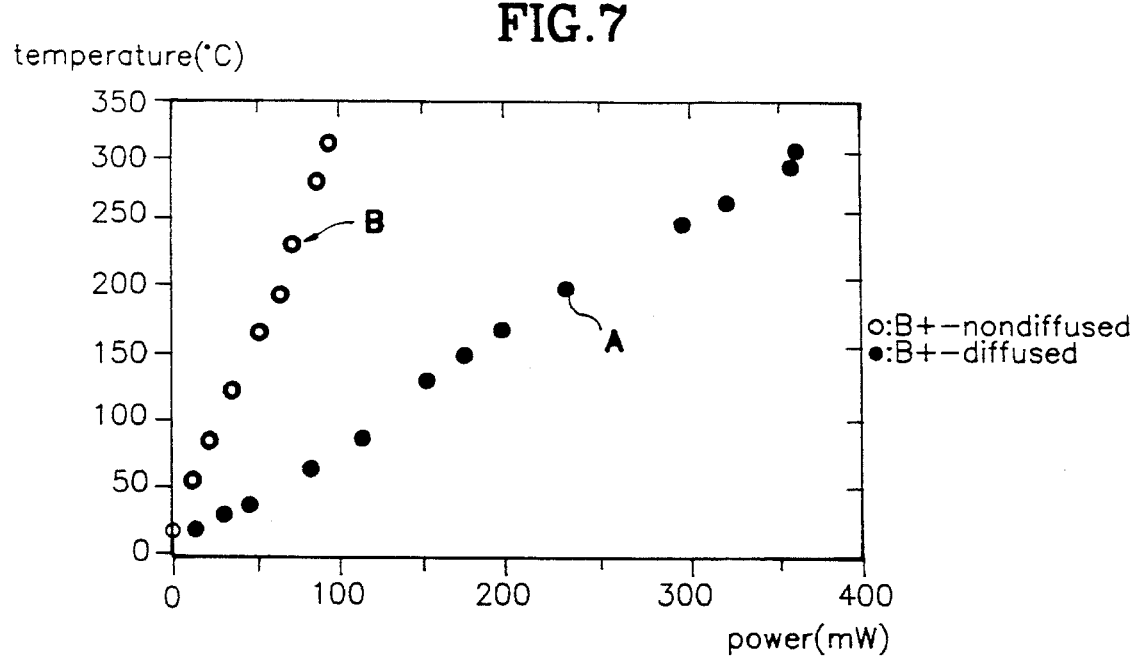
FIG. 7 is a graph showing the relationship between the power of heater and the temperature of gas sensing layer of the gas sensor shown in FIG. 4.

FIG. 7 shows the relationship between the power consumption of the heater and the temperature of the gas sensing layers. Dots A indicate the temperature of the gas sensing layers in accordance with the power of the heater of the device where boron is diffused to the silicon substrate as in the above process. Dots B indicate the temperature of the gas sensing layers in accordance with the power of the heater of the device manufactured with the boron diffusion step being excluded.

If boron is diffused, the silicon substrate is not fully removed and a portion where boron is diffused is left. In this case, a great amount of heat transmission is performed as compared with the case where boron is not diffused and the substrate is completely etched. With the same power of heater, the gas sensing layers are heated to a lower temperature than when boron is not diffused.

This indicates that a large amount of heat transmission is performed via the silicon substrate. In this invention, the back surface of the silicon substrate is etched so that the power consumption of heater can be reduced and the gas sensing layer be heated at an adequate temperature.

Here, since boron is diffused to the depth of 2 μm from the substrate surface, this does not affect the characteristics of device. Since the boron diffused layer serves as an etch stop together with the nitride layer, they form dual etch stops in etching the silicon substrate. This prevents the top of the device from being etched as well.

The gas sensitivity of the gas sensor manufactured as above is measured by an automatized gas characteristic measuring apparatus. The gas characteristic measuring apparatus is made up of a gas flow amount controller for controlling the flow amount of gas coming into from respective gas chambers, a mixer for mixing the gas whose flow amount is controlled, a chamber into which the mixed gas comes and to which a gas sensor is mountable, a vacuum pump for discharging various gases prior to and after measurement, an automatic pressure controller for maintaining a predetermined pressure in the chamber, and a computer for serially measuring and storing the characteristic change of the gas sensor by automatically controlling the measuring apparatus.

The gas sensitivity of the gas sensor measured by the measuring apparatus is indicated by the resistivity (%) of the gas sensor when the gas to be measured is present with respect to the resistance of the gas sensor in air. This can be given as the following equation.

$$Sensitivity(S) = (Ro-Rg) \times 100(\%)$$

where Ro is the resistance of gas sensor in air; and

Rg is the resistance of gas sensor when a gas to be measured is present.

Figure 8:
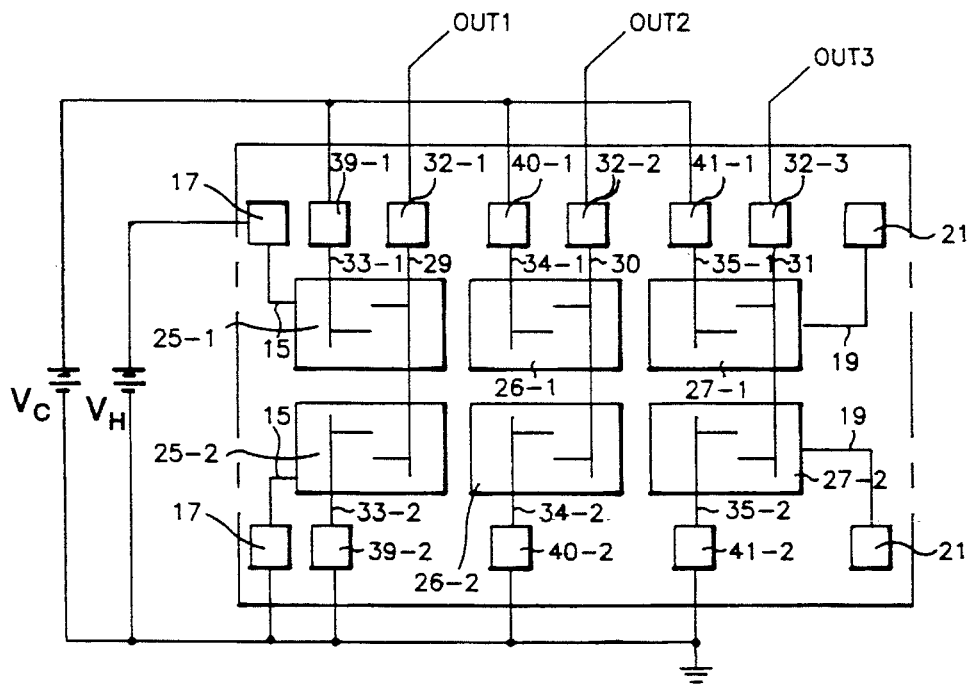
FIG. 8 is an example of a circuit for measuring the gas sensing characteristic by using a reference device of the gas sensor shown in FIG. 4 as a load resistor.

FIG. 8 illustrates an array of six gas sensors of FIG. 4, in which a serial circuit where a reference device where the gas shielding layer is formed on the gas sensing layer is used as a load device in sensing gas.

Figure 9A:
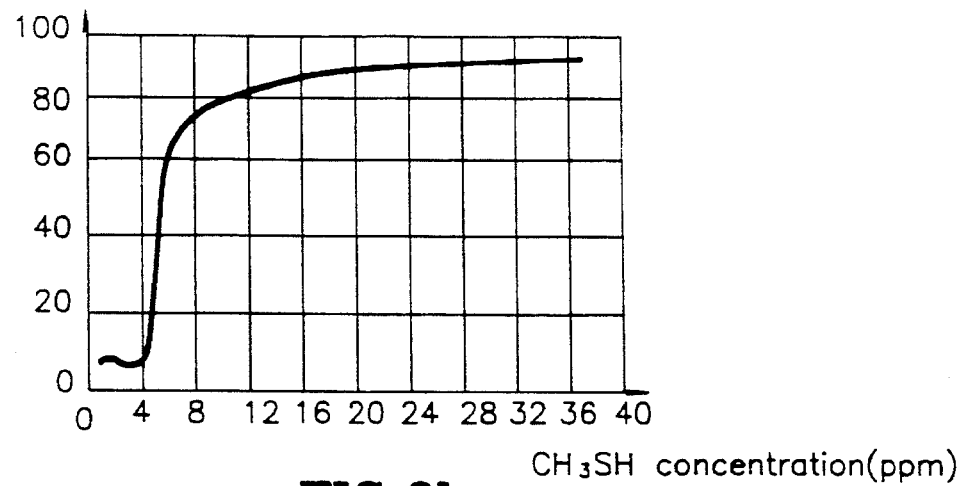
FIGS. 9a, 9b and 9c are graphs showing the gas sensing characteristic of the gas sensor of FIG. 4.
Figure 9B:
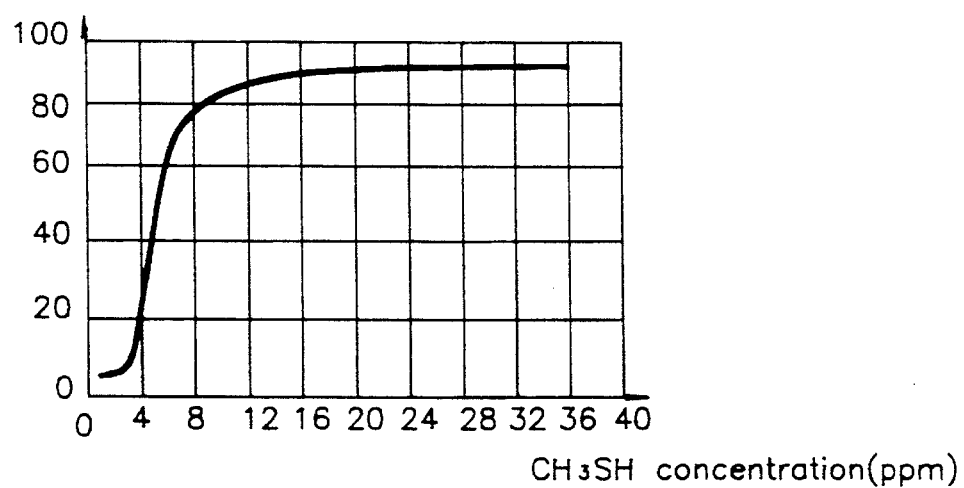
Figure 9C:
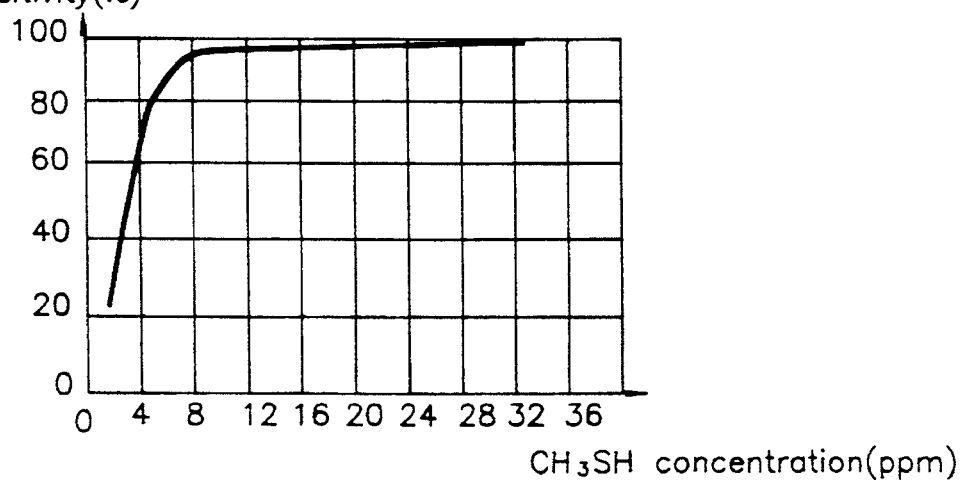

Referring to FIG. 8, when a predetermined voltage $V_H$ is applied to heater 15 via pad 19 which is then heated, a plurality of gas sensing layers thereon are heated at a predetermined temperature, thereby facilitating gas detection. Static voltage Vc is applied to electrodes (33-1,33-2), (34-1,34-2), and (35-1,35-2) of respective pairs of gas sensors via respective pads (39-1,39-2), (40-1,40-2) and (41-1,41-2) so that resistance values vary according to gas detection of the gas sensing layers and gas sensing characteristics thereof are measured in accordance with the variation of resistance values are output via first output port first output port OUT1, second output port OUT2, and third output port OUT3. Here, the gas sensing characteristics at the respective output ports are shown in FIGS. 9a, 9b and 9c.

In the conventional technology, in order to measure a resistance in accordance with the gas sensing by the gas sensor, a load resistor having the same value as the resistor of gas sensor is serially connected to the gas sensor to form a serial circuit. However, in this invention, as shown in FIG. 8, since the gas sensor where the gas shielding layer is formed, having the same characteristic and material as those of the gas sensor for detecting gas, is used for the load resistor, the variation of the initial resistance value due to the variation of external environment can be prevented.

If the initial value of gas sensor is changed due to external environment, the initial value of the load resistor serving as a reference device having the same characteristics as the sensor is varied so that the gas sensor is not affected by external environment. This enables the kind and concentration of gas to be precisely measured.

Figure 10:
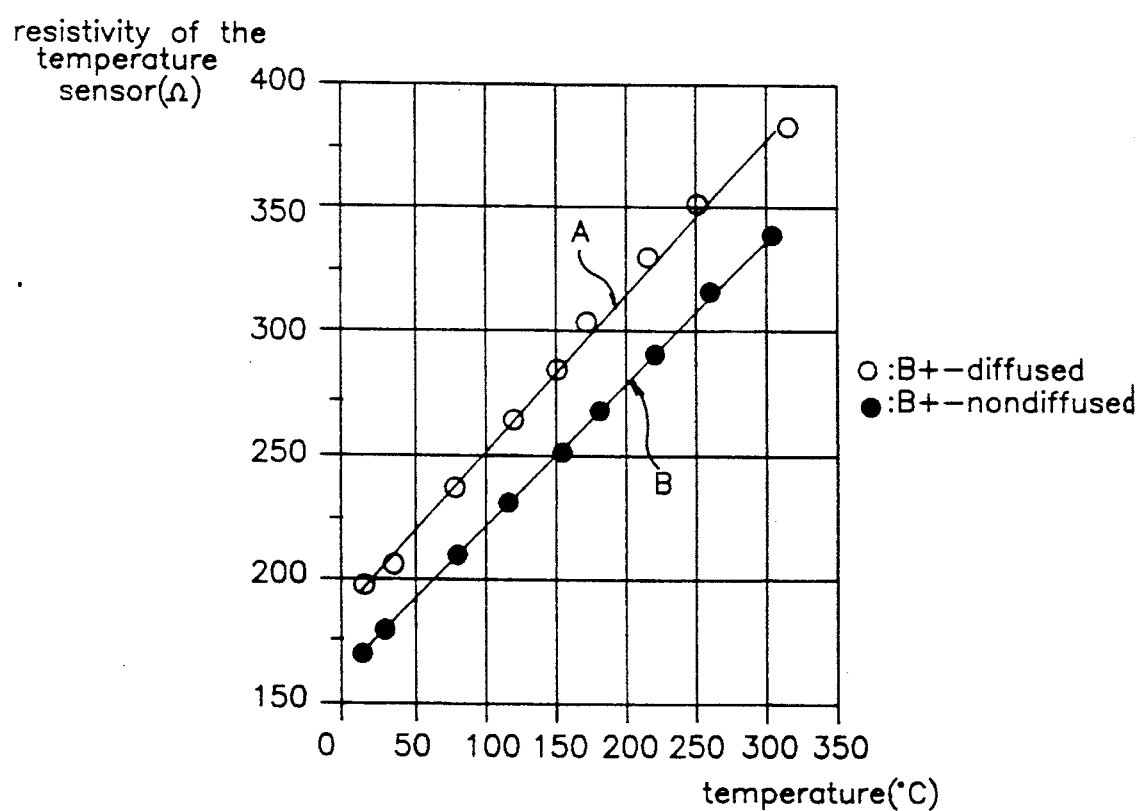
FIG. 10 is a graph showing the relationship between the temperature of heater and the resistance of temperature sensor of the gas sensor of FIG. 4.

FIG. 10 illustrates the temperature characteristic of the thin-film gas sensor of the present invention, especially showing the relationship between the temperature of the heater and the resistance of the temperature sensor. In FIG. 10, similar to FIG. 6, dots A indicate the characteristics of temperature sensor of device where boron is diffused. Dots B indicate the characteristics of temperature sensor of device where a step of boron diffusion is excluded.

The thin-film gas sensor has a resistance value decreased as the temperature increases. At the same temperature of heater, the resistance value of the temperature sensor is greater when boron is diffused than when boron is not diffused. In other words, similar to FIG. 7, when part of the substrate where boron is diffused is left, heat transmission is performed through the substrate and the resistance value of temperature sensor becomes greater, as compared with when the substrate is completely etched.

Since a device reacting to gas and a device not reacting to gas are both present on one chip in the gas sensor, the device not reacting to gas can be used for the load resistor. When the reference device is used as the load resistor, the resistance of gas sensor and the load resistance are the same automatically. This is because the gas sensor and load resistor are manufactured of the same material and under the same conditions on the same support layer, and respond together, to external environment such as room temperature, the temperature of the support layer, and the intensity of light.

However, since the gas shielding layer for precluding gas reaction is present in the reference device, such a circuit outputs only with a detected gas. This greatly reduces errors created due to the external environment. Further, since there is no variation in the initial value occurring as usage duration increases, the circuit is easy to employ in a pattern recognition method. Accordingly, the circuit finds out the kind of gas and effectively detects the precise concentration of gas.

It is made possible to simply and ideally form a bridge circuit which is one of the detecting circuits of the gas sensor. Since a reference device essentially employed in the bridge circuit is manufactured with the same thing as that of the gas sensor, this enables an ideal reference device to be realized. Further, the gas sensor and reference device are electrically connected on the same chip, thereby simply forming the bridge circuit.

Figure 11:
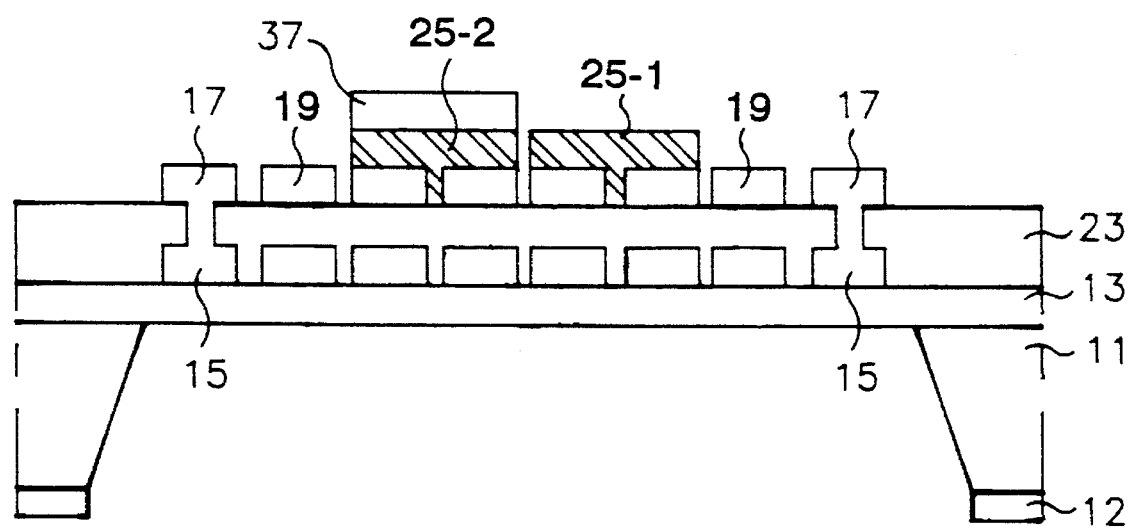
FIG. 11 illustrates the cross-sectional structure of another embodiment of the thin-film gas sensor of the present invention.

FIG. 11 is a cross-sectional view of another embodiment of the thin-film gas sensor of the present invention.

Referring to FIG. 11, in another embodiment of the thin-film gas sensor of the present invention, heater 15 is formed on insulating layer 13 for support and temperature sensor 19 is formed on interlayer insulating layer 23. In the first embodiment of FIGS. 4 and 5, however, temperature sensor 19 and heater 15 are both formed on insulating layer 13 for support.

Specifically, the thin-film gas sensor comprises a silicon substrate 11 of a diaphragm structure, a support layer 13 formed on silicon substrate 11, a heater 15 for heating a gas sensing layer at different temperatures, a temperature sensor 19 for precisely controlling the temperature of the heater, a plurality of electrodes for reading out the signal of the gas sensor, and a plurality of gas sensing layers having different operation temperatures and for detecting different gases on the electrodes.

FIGS. 13a–13l illustrate a manufacturing process of the second embodiment of the thin-film gas sensor of the present invention.

Referring to FIG. 13a, a silicon substrate is p-type 100. Both sides of the silicon substrate are polished so that the thickness of the silicon substrate is about 400 μm. Referring to FIG. 13b, boron is diffused to the depth of 2 μm from the surface of the substrate on the front surface of the polished silicon substrate.

Referring to FIG. 13c, insulating layers are uniformly deposited on both sides of the silicon substrate by the thickness of 3,000 Å by LPCVD. Here, nitride layers are used for the insulating layers. Nitride layer 13 formed on the front surface of the substrate through which boron is injected acts as a support layer, whereas nitride layer 12 formed on the back surface of the substrate acts as an etching mask in a succeeding etching step of the silicon substrate.

Referring to FIG. 13d, a photoresist layer (not shown) is coated on insulating layer 13 and photolithographed so that the photoresist layer on a portion where the heater is formed is removed to expose the substrate where the heater is formed. Then, tantalum which is excellent in adhering to the nitride layer is deposited by the thickness of 500 Å under 7.5 mmT of pressure by sputtering, and platinum is deposited as thick as 4,500 Å. The silicon substrate where tantalum and platinum are deposited is immersed into aceton so that unnecessary tantalum and platinum are removed by lift off using ultrasonic waves. By doing this, the heater is formed only on the exposed substrate where the photoresist layer is removed.

FIGS. 12a and 12b are plan views of the heater of the present invention.

In FIG. 12a, the width of line of the heater and the distance between the lines of the heater are the same. In FIG. 12b, the width of line of the heater and the distance between the lines of the heater are different.

With the heater of FIG. 12a, gas sensing layers of a plurality of the gas sensors of FIG. 4 can be heated at the same temperature. The heater of FIG. 12b can heat gas sensing layers of a plurality of the gas sensors at different temperatures.

In order for different gas sensing layers to have different operation temperatures, as shown in FIGS. 12a and 12b, the width of lines of heater or the distance between the lines of heater may be formed to be different.

This invention suggests three types of the heater for heating a plurality of gas sensing layers at different temperatures. The difference of temperature of heater formed on the same support layer is determined by the rate of power consumed.

In the first type of heater, width W of lines of heater are differently formed so that if the same amount of current flows, different voltages are applied in accordance with the width of lines of heater. This makes the temperature of heater different. Specifically, in a portion where width $W_2$ of line is narrower, the resistance of heater is greater and therefore higher voltage is applied so that the heater heats the gas sensing layer at a high temperature. In a portion where width $W_1$ of line is wider, the resistance of heater is lower and the voltage is also lower so that the gas sensing layer is heated at a low temperature.

In the second type of heater, the width of line of heater is kept constant and distance D of lines of heater is different so that the heater has different temperatures. In a portion where distance D2 between lines is narrower, the temperature of heater is higher, whereas in a portion where distance d1 between lines of heater is wider, the gas sensing layer can be heated at different operation temperatures.

In the third type of heater, as shown in FIG. 12a, the first and second types are mixed. The line width of heater and line distance of heater are simultaneously controlled, thereby efficiently generating different temperatures.

By appropriately using the above types, different temperatures can be accomplished on the same support layer.

In order to insulate the heater and the temperature sensor formed after the manufacturing of heater, interlayer insulating layer 23 is deposited on the front surface of the substrate where the heater is formed, as thick as 6,000 Å by sputtering as shown in FIG. 13e.

FIG. 13f illustrates a step of forming a contact hole for pad. Interlayer insulating layer 23 where the pad is to be formed by dry etching is removed to thereby form contact hole 16 on heater 15.

Figure 13H:
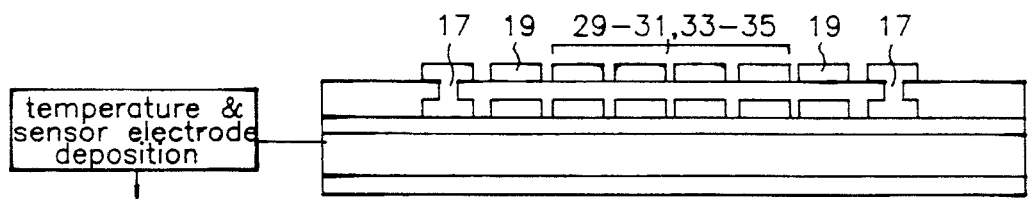
Figure 13I:
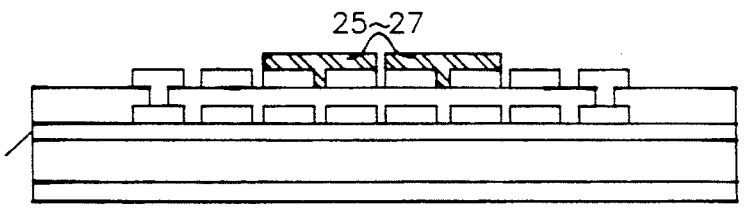

As shown in FIGS. 13g and 13h, pad 17 for heater, temperature sensor 19, electrodes (29–31) and (33–35) are photolithographed in the same manner as that of the heater. Then, tantalum and platinum are deposited as thick as 500 Å and 4,500 Å by sputtering and removed by lift off.

By forming the pad, temperature sensor and electrodes, a metallization is finished. The result is thermally treated at 300°–800° C. under $N_2$ atmosphere for 30 minutes so that the structure of metal becomes dense and the resistance value is lowered for smooth flow of current.

Subsequently, gas sensing layers 25–27 are formed on the electrodes by using the gas sensing material manufactured in the sputtering target step. Similar to the first embodiment, the method of forming the gas sensing layers is that first, the gas sensing material where $Al_2O_3$ is added to ZnO by 0–30% is deposited as thick as thousands of Å by sputtering after photolithography. The ZnO gas sensing layer is removed by lift off, while a necessary portion on the electrodes is left. The result is thermally treated at 500°–800° C. for several hours in air so that the structure of the gas sensing layer becomes dense and reaction on detected gas is easy.

Near the ZnO gas sensing layer, a gas sensing material where Pd is added to $SnO_2$ and $WO_3$ by 0–10% is deposited by sputtering in the same manner as when the ZnO gas sensing layer is formed, and thermally treated to thereby form a gas sensing layer of $SnO_2$ and $WO_3$.

Figure 13J:
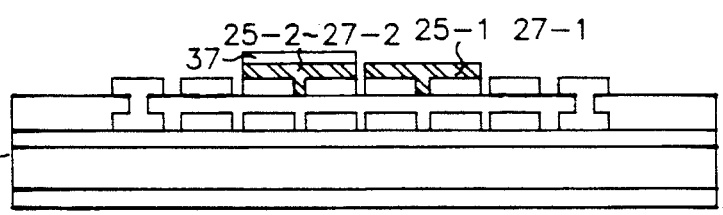

Sequentially, as shown in FIG. 13j, after photolithography, the nitride layer is deposited as thick as 10,000 Å by sputtering and removed by lift off to thereby form a gas shielding layer 37 on the gas sensing layer to function as a reference device.

After the process performed on the front surface of the substrate, in order to minimize the power consumption of heater, the back surface of the substrate is etched. Therefore, since the silicon substrate of a higher heat conductivity than the support layer is removed, the heat transmission to the side or bottom of the device can be shielded. This minimizes the power consumption of heater, resulting in efficiently heating the gas sensing layer at a necessary operation temperature.

Figure 13K:
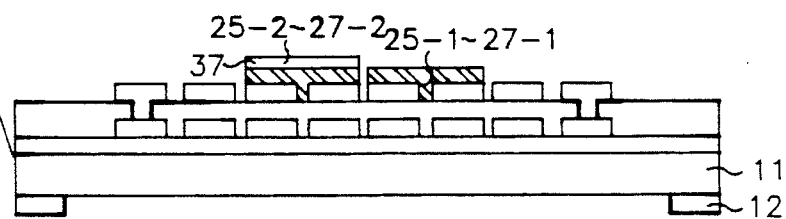

According to the etching method of the back surface of the silicon substrate, insulating layer 12 formed on the back surface of the substrate is removed by dry etching, thereby exposing the surface of the substrate to be etched as shown in FIG. 13k.

Figure 13L:
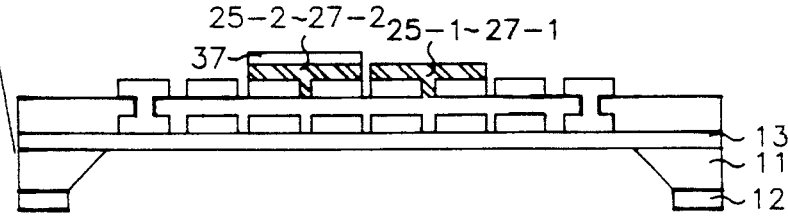
Figure 13L:
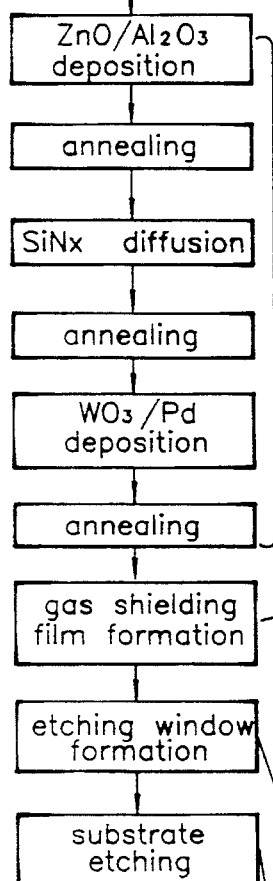
Figure 14A:
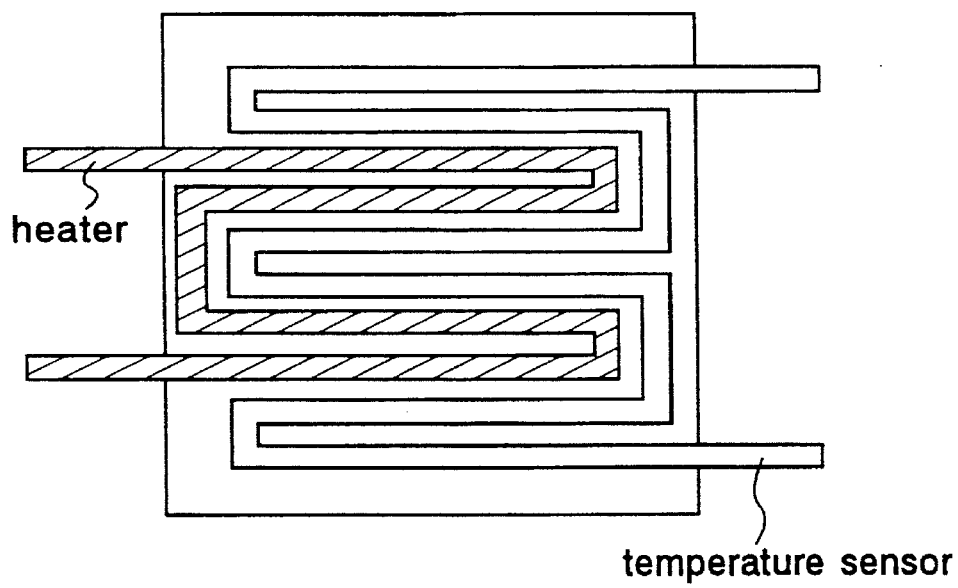
FIGS. 14a and 14b illustrate the arrangement of the heater and temperature sensor.
Figure 14B:
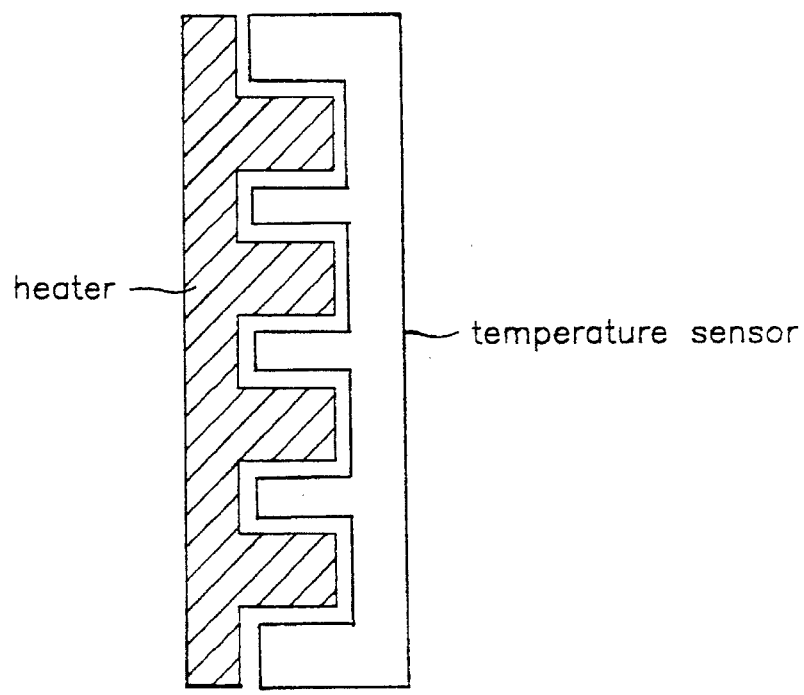

As shown in FIG. 13l, the exposed substrate is etched in KOH solution of an excellent selectivity to the nitride layer, an insulating layer, by anisotropic etching for 5 or 6 hours, with the nitride layer being as a mask.

As described above, the thin-film gas sensor of the present invention has the following effects.

First, a conventional thick ceramic substrate such as alumina is not used, but in this invention, a silicon nitride layer which is very thin and has a low heat conductivity is used for a support layer, thereby minimizing loss of heat.

Therefore, the gas sensing layer is maintained at an adequate temperature with low power consumption so that the false operation of gas sensor caused by the nonuniformity of temperature is reduced, thereby greatly enhancing reliability.

Further, since there is no phenomenon of locally high temperature, the deterioration of the gas sensing layer can be reduced so that the life of the gas sensor is prolonged and the response characteristics of device are enhanced.

Second, for heating several devices to having various operation temperatures, a single heater, not individual heaters, is formed on the support layer so that several devices can be heated at the same time, thereby simplifying the manufacturing process. Also, there is no need of using several large power devices in driving a gas sensor of a small array, thereby reducing the volume of device and power consumption of heater, and facilitating a wire bonding step.

Third, in the subject array thin-film gas sensor, a reference device of the same condition is used for a load resistor so that the initial resistance value does not vary due to external environment. Further, the kind of gas and concentration of gas can be effectively detected, thereby providing a reliable gas sensor without false operation.

What is claimed is:

1. A thin-film gas sensor comprising:

a silicon substrate;

an insulating layer formed on a surface of said silicon substrate;

a heater of a plurality of lines in zigzag on a first region of a surface of said insulating layer, each of said lines being connected to adjacent lines;

a temperature sensor formed in zigzag on a second region of the surface of said insulating layer, a loop of heaters in zigzag on the first region and a loop of temperature sensors in zigzag on the second region being arranged in the same plane side by side with each other;

an interlayer insulating layer for electrically insulating said heater and temperature sensor;

a plurality of electrodes formed on said interlayer insulating layer;

a plurality of pairs of gas sensing layers disposed in an array on said electrodes and for reacting to detected gas; and a plurality of gas shielding layers each formed on one gas sensing layer out of said pair of gas sensing layers.

2. A thin-film gas sensor as claimed in claim 1, wherein said heater and said temperature sensor are made of dual metal layer of platinum and tantalum.

3. A thin-film gas sensor as claimed in claim 1, wherein, of a pair of gas sensing layers, one gas sensing layer is a reference device and one gas sensing layer is a gas sensing portion, both are made of the same gas sensing material.

4. A thin-film gas sensor as claimed in claim 3, wherein, the gas sensing layer acting as the reference device is used for a load resistor.

5. A thin-film gas sensor as claimed in claim 1, wherein said plurality of electrodes comprise:

a plurality of common electrodes commonly connected to the gas sensing layer where the gas shielding layer is not formed and to the gas sensing layer where the gas shielding layer is formed;

a plurality of first electrodes connected to the gas sensing layer where the gas shielding layer is not formed; and a plurality of second electrodes connected to the gas sensing layer where the gas shielding layer is formed.

6. A thin-film gas sensor as claimed in claim 5, wherein said respective electrodes are made of dual metal layer of platinum and tantalum.

7. A thin-film gas sensor as claimed in claim 1, wherein said plurality of gas sensing layers have different operation temperatures.

8. A thin-film gas sensor as claimed in claim 7, wherein a distance between lines of said heater is kept constant, and lines of said heater provided under said pair of gas sensing layers having a higher operation temperature are narrower than lines of said heater provided under said pair of gas sensing layers having a lower operation temperature.

9. A thin-film gas sensor as claimed in claim 7, wherein a width of lines of said heater is kept constant, and distances between lines of said heater provided under said pair of gas sensing layers having a higher operation temperature are narrower than distances between lines of said heater provided under said pair of gas sensing layers having a lower operation temperature.

10. A thin-film gas sensor as claimed in claim 7, wherein said heater has narrower line width and line distance under said pair of gas sensing layers having a higher operation temperature, and has broader line width and line distance under said pair of gas sensing layers having a lower operation temperature.

11. A method of manufacturing a thin-film gas sensor comprising the steps of:

forming an insulating layer on both sides of a silicon substrate;

simultaneously forming a heater and a temperature sensor formed in zigzag on said insulating layer on the front surface of said silicon substrate;

forming an interlayer insulating layer on said insulating layer where said temperature sensor and said heater are formed;

forming a contact hole by exposing part of said heater and said temperature sensor;

forming a pad for heater and a pad for temperature sensor on said interlayer insulating layer so that said contact hole comes into contact with said heater and said temperature sensor;

forming a plurality of electrodes on said interlayer insulating layer excluding a portion where said pad for heater and said temperature sensor are formed;

forming a plurality of pairs of gas sensing layers in an array form, on said interlayer insulating layer including said electrodes;

forming a gas shielding layer only on one gas sensing layer of said respective pairs of gas sensing layers;

etching said insulating layer formed on the back surface of said substrate, thereby exposing the insulating layer to the substrate; and etching the exposed substrate with said insulating layer being as a mask.

12. A method of manufacturing a thin-film gas sensor as claimed in claim 11, further comprising, prior to the step of forming said insulating layer on said substrate, a step of forming a boron diffused layer by diffusing boron through said substrate.

* * * * *